US010551332B2

(12) United States Patent
Chan et al.

(10) Patent No.: US 10,551,332 B2
(45) Date of Patent: Feb. 4, 2020

(54) APPARATUS FOR DETERMINING THE CONGEALING POINT OF A PETROLEUM WAX SAMPLE AND METHODS THEREFOR

(71) Applicant: ExxonMobil Research and Engineering Company, Annandale, NJ (US)

(72) Inventors: Joseph Chan, Sarnia (CA); Elizabeth Turner, Sarnia (CA)

(73) Assignee: ExxonMobil Research and Engineering Company, Annandale, NJ (US)

( * ) Notice: Subject to any disclaimer, the term of this patent is extended or adjusted under 35 U.S.C. 154(b) by 289 days.

(21) Appl. No.: 15/352,090

(22) Filed: Nov. 15, 2016

(65) Prior Publication Data

US 2017/0160217 A1    Jun. 8, 2017

Related U.S. Application Data

(60) Provisional application No. 62/262,959, filed on Dec. 4, 2015.

(51) Int. Cl.
*G01N 25/02* (2006.01)
*G01N 25/04* (2006.01)

(52) U.S. Cl.
CPC .................. *G01N 25/04* (2013.01)

(58) Field of Classification Search
CPC .................................................... G01N 25/04
See application file for complete search history.

(56) References Cited

U.S. PATENT DOCUMENTS

| 5,015,357 | A | * | 5/1991 | Rueff | C10G 73/36 |
| | | | | | 208/30 |
| 5,447,374 | A | * | 9/1995 | Fraser | B01L 3/50825 |
| | | | | | 215/227 |
| 6,212,776 | B1 | * | 4/2001 | Izumi | B26B 19/14 |
| | | | | | 30/43.4 |
| 2010/0193345 | A1 | * | 8/2010 | Carl | B01D 3/085 |
| | | | | | 202/238 |

FOREIGN PATENT DOCUMENTS

CN    201170784 U   Y    12/2008

OTHER PUBLICATIONS

CN101738410 EPO translation (Year: 2010).*

* cited by examiner

*Primary Examiner* — Lisa M Caputo
*Assistant Examiner* — Nasir U. Ahmed
(74) *Attorney, Agent, or Firm* — Robert A. Migliorini; Scott F. Yarnell

(57) ABSTRACT

An apparatus for determining the congealing point of a wax-containing sample, the sample placed within a sample flask. The apparatus includes a motor having a rotatable shaft extending horizontally therefrom; clamp for mounting the sample flask thereto, the clamp operatively connected to the rotatable shaft; and a temperature sensor for determining sample temperature over time. A method for determining the congealing point of a wax-containing sample is also provided.

10 Claims, 5 Drawing Sheets

APPARATUS FOR DETERMINING THE CONGEALING POINT OF A PETROLEUM WAX SAMPLE AND METHODS THEREFOR

CROSS-REFERENCE TO RELATED APPLICATIONS

This application claims priority to U.S. Provisional Application Ser. No. 62/262,959 filed Dec. 4, 2015, which is herein incorporated by reference in its entirety.

FIELD

The present disclosure relates to an apparatus and methods for determining the congealing point of a sample.

BACKGROUND

Waxes are organic substances that tend to be solid at ambient temperature and become free-flowing at elevated temperatures. While the chemical composition of waxes may be complex, normal alkanes are present. Also, the molecular weight distributions of waxes tend to be wide. The main commercial source of wax is crude oil, but not all crude oil refiners produce wax. Mineral waxes can also be produced from lignite. Plants, animals and even insects produce materials sold in commerce as wax.

Paraffin and microcrystalline waxes are derived from petroleum. They are easy to recover and offer a wide range of physical properties that can often be tailored by refining processes. Most producers offer two distinct types of petroleum waxes: paraffins, which are distinguished by large, well formed crystals; and microcrystallines, which are higher melting waxes with small, irregular crystals. Microcrystalline wax contains substantial proportions of branched and cyclic saturated hydrocarbons in addition to normal alkanes.

Some producers also sell "intermediate" wax, in which the boiling range is cut where the transition in crystal size and structure occur. Petroleum wax producers also characterize wax by degree of refinement; fully refined paraffin has oil content generally less than 0.5%, and fully-refined microcrystalline less than 3%. Slack wax, precursors to the fully refined versions in either case, tend to have oil content above 3%, and as high as 35% by weight. Paraffin wax produced from petroleum is essentially a pure mixture of normal and iso-alkanes without the esters, acids, etc. found in the animal and vegetable-based waxes.

Synthetic waxes have entered the wax market in the recent past. Polyethylene waxes are low molecular weight polyethylenes (less than 10,000 Mn) having wax-like properties made by either high-pressure or low-pressure (Zeigler-type catalyst) polymerization. All such waxes have the same basic structure, but the various production processes yield products with distinctly different properties, and these have a major impact on the use of products. Products from one manufacturer may satisfy one particular application, while product from a similar process will not work well.

Fischer-Tropsch (FT) wax is a synthetic wax produced by the polymerization of carbon monoxide under high pressure, a technology used in the emerging natural gas to liquid (GTL) projects. The hydrocarbon product of FT reaction is distilled to separate the mix into fuels products and waxes with melting points ranging from about 45-106° C. It has been estimated that recent synthetic wax consumption in North America was 420 million lbs., of which FT wax accounts for about 195 million lbs.

Alpha olefin waxes are synthetically derived from ethylene via a Ziegler-Natta catalyst. The process results in a Schulz-Flory distribution of alpha olefins ranging from $C_4$ through $C_{30+}$. These are distilled into the individual carbon fractions or carbon fraction blends. Due to the high melting points of the waxes, $C_{20}$ and higher carbon numbers are fractionated into blends. Because of the linear double bond present in normal alpha olefins, these waxes can be functionalized or reacted to create other derivatives. They can also be used for their physical properties such as hardness and melting point. End uses for alpha olefin waxes include lube oil additives, PVC lubricants, candles, oilfield chemicals and personal care applications.

Montan wax is derived by solvent extraction of lignite. The earliest production of montan wax on a commercial scale was in Germany during the latter half of the nineteenth century. Germany continues to lead the world in production of montan wax; although some montan wax is produced in the United States from the Ione lignite bed in California. The composition of montan wax varies geographically with production, but includes varying amounts of wax, resin and asphalt. Other mineral waxes include peat waxes, ozokerite and ceresin waxes.

Congealing point is a wax property that is of interest to many petroleum wax consumers. The congealing point represents the temperature at which a sample being cooled develops a "set" or resistance to flow. At that temperature, the wax may be at or close to the solid state, or it may be semisolid and quite unctuous, depending on the composition of the wax or petrolatum being tested. In the case of petrolatum, the congealing property is associated with the formation of a gel structure as the sample cools.

Historically, the congealing point of waxes has been determined by manually conducting standardized test procedures, such as ASTM Test Method D938, Standard Test Method for Congealing Point of Petroleum Waxes, Including Petrolatum, or TAPPI Test Method T-662, Congealing Point of Petroleum Waxes Including Petrolatum. As is known by those skilled in the art, ASTM Test Method D938 is an alternative to ASTM Test Method D127. The results obtained using ASTM Test Method D938 are usually lower than the results obtained by Test Method D127, the amount of the deviation varying with the nature of the petroleum wax.

ASTM Test Method D938 and TAPPI Test Method T-662 are manual test methods that require an operator to be exposed to multiple risks. These risks include the handling of hot glassware for an extended period, often three to eight consecutive minutes, depending on the sample; the use of a liquid-in-glass thermometer for an extended period; and the possibility of incurring a repetitive stress injury (RSI) risk, if multiple samples are to be tested. This is due to the fact that the operator must constantly reset his or her wrists to rotate an Erlenmeyer flask.

Therefore, what is needed is an automated test apparatus for determining the congealing point of a sample that reduces exposure to hot glassware, liquid-in-glass thermometers, and RSI risks, while yielding an acceptable level of test precision.

SUMMARY

In one aspect, disclosed herein is an apparatus for determining the congealing point of a wax-containing sample, such as a petroleum wax-containing sample, the sample placed within a sample flask, comprising: a) a motor having a rotatable shaft extending horizontally therefrom; b) a clamp for mounting the sample flask thereto, the clamp operatively connected to the rotatable shaft; and c) a temperature sensor for determining sample temperature overtime.

In some embodiments, the apparatus also includes a housing for mounting the motor within.

In some embodiments, the apparatus also includes a power switch for permitting a source of power to be supplied to the motor.

In some embodiments, the source of power is alternating current. In some embodiments, the source of power is direct current. In some embodiments, the source of direct current is a battery. In some embodiments, the battery is mounted with the housing.

In some embodiments, the apparatus also includes an indicator to indicate when power is supplied to the motor.

In some embodiments, the motor is structured and arranged to rotate the clamp at a speed of less than 50 RPM.

In some embodiments, the motor is structured and arranged to rotate the clamp at a speed of between about 20 RPM and about 30 RPM.

In another aspect, disclosed herein is a semi-automated method for determining the congealing point of a wax-containing sample, such as a petroleum wax-containing sample. The method includes: (a) heating a sample flask to a predetermined temperature in a heating unit; (b) heating the wax-containing sample to the predetermined temperature in the heating unit; (c) immersing a temperature sensor in the wax-containing sample; (d) removing the sample flask from the heating unit; (e) removing the temperature sensor from the wax-containing sample, while retaining in adherence thereto a droplet of the wax-containing sample; (f) inserting the temperature sensor into the sample flask; (g) inserting the sample flask into a mounting clamp of an apparatus for determining the congealing point of a wax-containing sample, the apparatus including a motor having a rotatable shaft extending horizontally therefrom, the mounting clamp operatively connected to the rotatable shaft; (h) providing a source of power to the motor to rotate the sample flask; (i) monitoring the temperature as the sample flask rotates; and (j) identify the temperature at which the wax-containing sample congeals.

In some embodiments, the method also includes repeating steps (a)-(j).

In some embodiments, the apparatus further includes a power switch for providing the source of power to be supplied to the motor.

In some embodiments, the source of power is alternating current. In some embodiments, the source of power is direct current. In some embodiments, the source of direct current is a battery.

In some embodiments, the motor rotates the clamp at a speed of less than 50 RPM.

In some embodiments, the motor rotates the clamp at a speed of between about 20 RPM and about 30 RPM.

In some embodiments, the repeatability of the method is at least about 0.5° C. for petroleum distillate wax-containing samples and at least about 1.0° C. for residual wax-containing samples.

In some embodiments, the reproducibility of the method is at least about 1.5° C. for petroleum distillate wax-containing samples and at least about 2.5° C. for residual wax-containing samples.

DETAILED DESCRIPTION

All numerical values within the detailed description and the claims herein are modified by "about" or "approximately" the indicated value, and take into account experimental error and variations that would be expected by a person having ordinary skill in the art.

In FIGS. 1-5, like numerals denote like, or similar, structures and/or features; and each of the illustrated structures and/or features may not be discussed in detail herein with reference to the figures. Similarly, each structure and/or feature may not be explicitly labeled in the figures; and any structure and/or feature that is discussed herein with reference to the figures may be utilized with any other structure and/or feature without departing from the scope of the present disclosure.

In general, structures and/or features that are, or are likely to be, included in a given embodiment are indicated in solid lines in the figures, while optional structures and/or features are indicated in broken lines. However, a given embodiment is not required to include all structures and/or features that are illustrated in solid lines therein, and any suitable number of such structures and/or features may be omitted from a given embodiment without departing from the scope of the present disclosure.

FIGS. 1-5 provide illustrative, non-exclusive examples of apparatus, systems and methods for determining the congealing point of a wax-containing sample, such as a petroleum wax-containing sample, according to the present disclosure, together with elements that may include, be associated with, be operatively attached to, and/or utilize such apparatus, systems and methods.

Although the approach disclosed herein can be applied to a variety of sample test methods, the present description will primarily be directed to apparatus and methods for determining the congealing point of a wax-containing sample, such as a petroleum wax-containing sample.

Figure 1:
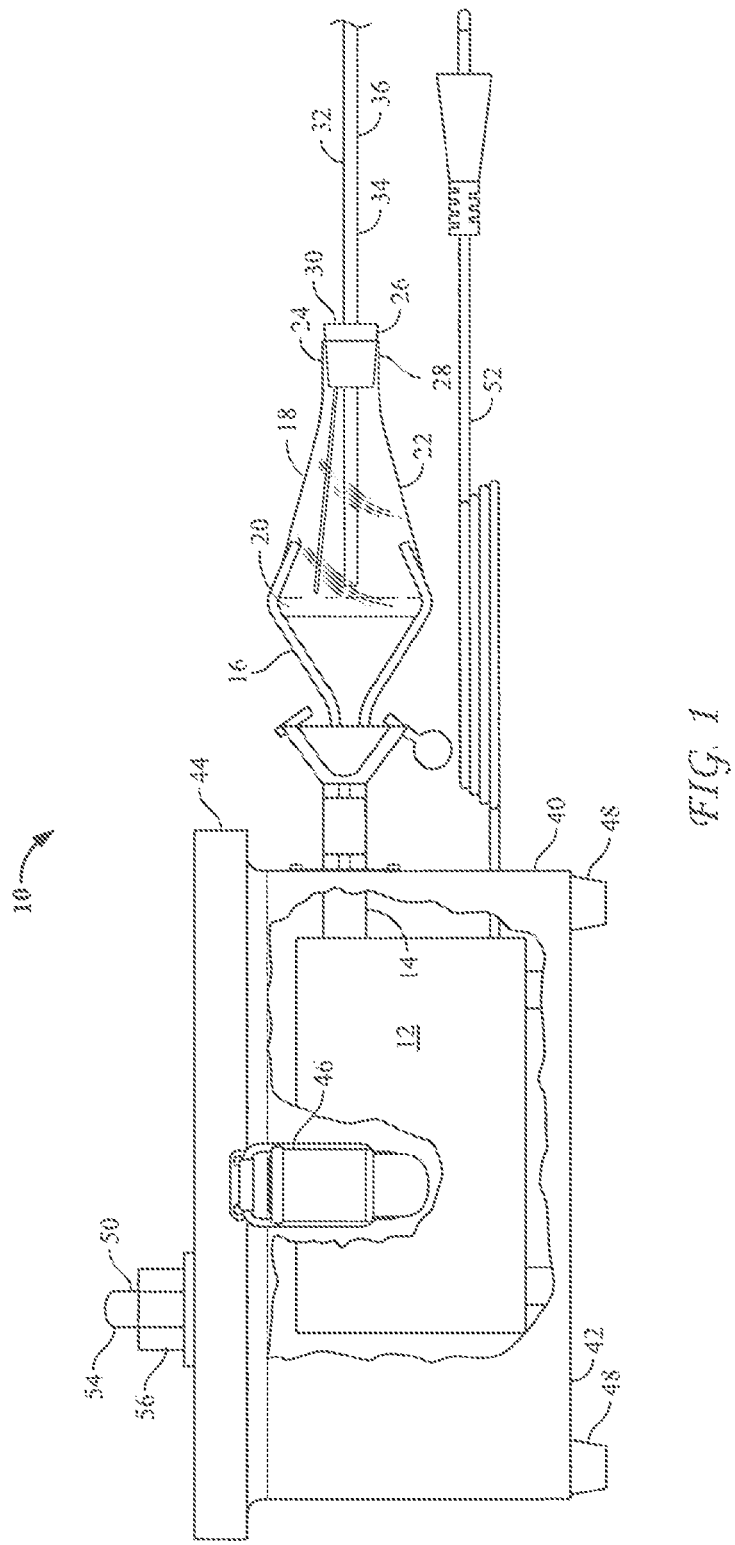
FIG. 1 presents a front plan view of an illustrative, nonexclusive example of an apparatus for determining the congealing point of a wax-containing sample, such as a petroleum wax-containing sample, according to the present disclosure.
Figure 2:
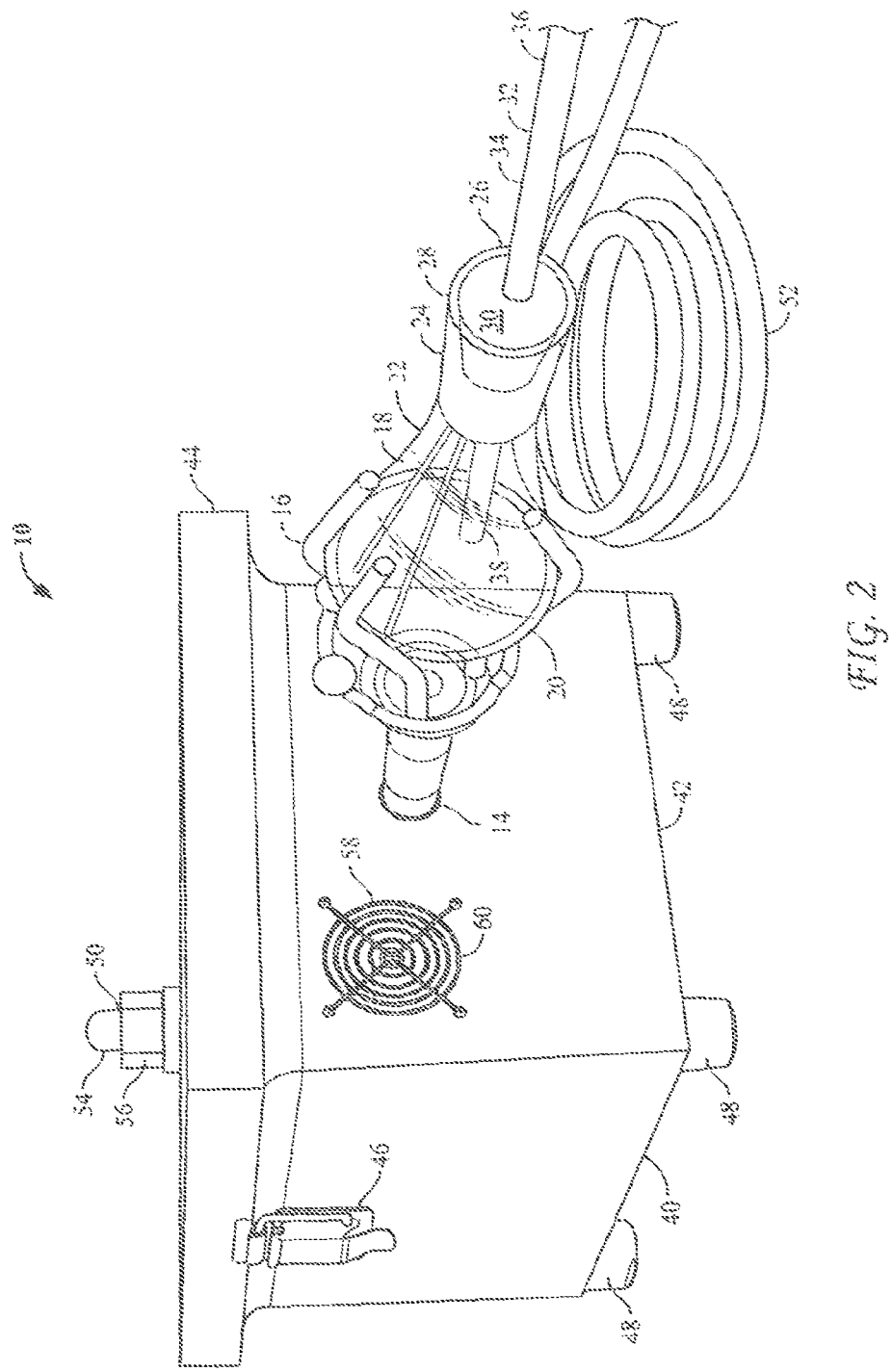
FIG. 2 presents a perspective view of the illustrative, nonexclusive example of an apparatus for determining the congealing point of a wax-containing sample, such as a petroleum wax-containing sample, according to the present disclosure.
Figure 3:
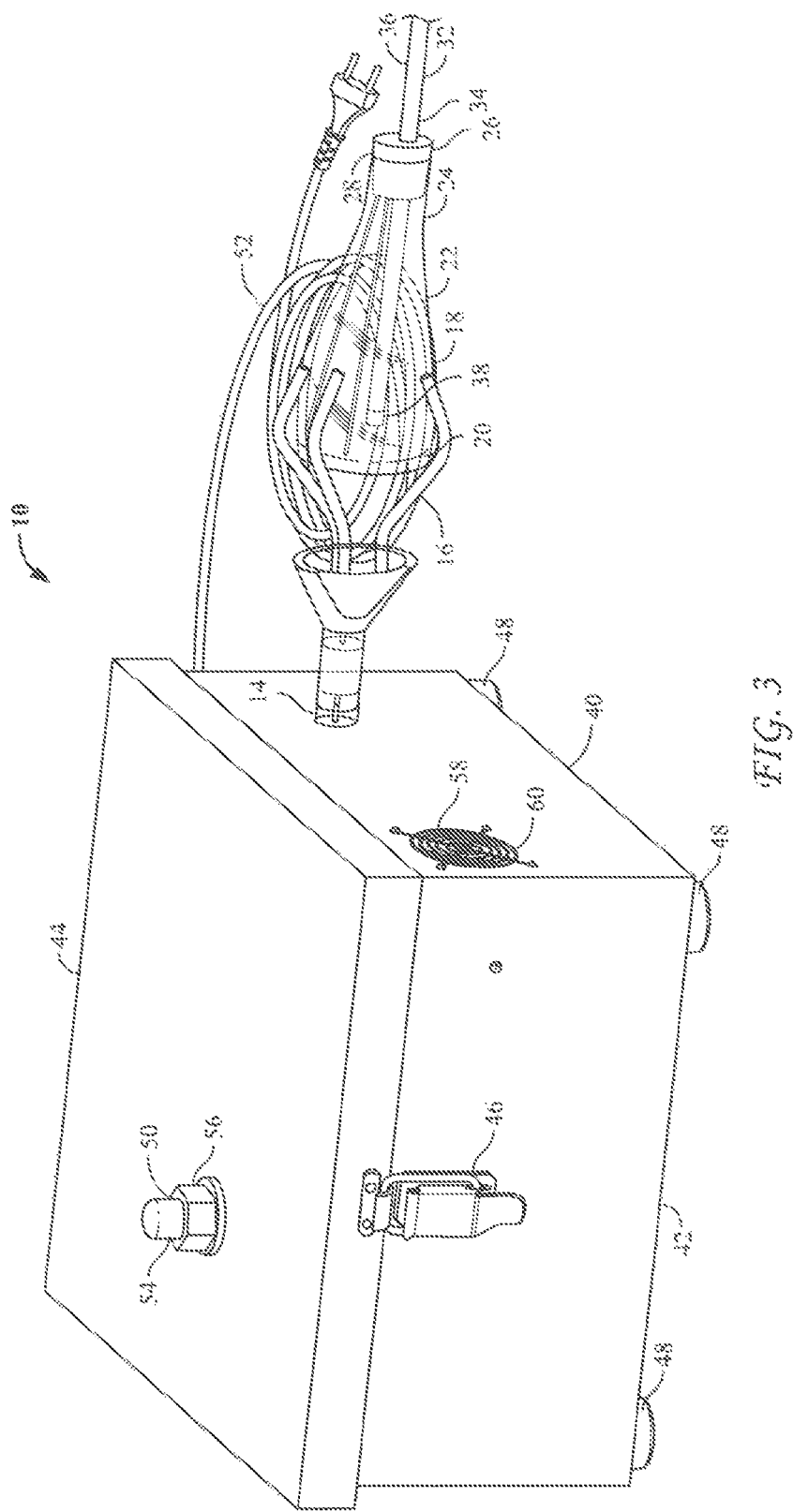
FIG. 3 presents a front perspective view of the illustrative, nonexclusive example of an apparatus for determining the congealing point of a wax-containing sample, such as a petroleum wax-containing sample, according to the present disclosure.

Referring now to FIGS. 1-3, an illustrative, nonexclusive example of an apparatus 10 for determining the congealing point of a wax-containing sample, such as a petroleum wax-containing sample, according to the present disclosure, is presented. Referring especially to FIG. 1, the apparatus 10 for determining the congealing point of a wax-containing sample, such as a petroleum wax-containing sample, includes a motor 12 having a rotatable shaft 14 extending horizontally therefrom. Apparatus 10 also includes a clamp 16 for mounting a flask 18 thereto. As shown, the clamp 16 is operatively connected to the rotatable shaft 14 of the motor 12.

In some embodiments, flask 18 may be an Erlenmeyer flask 18. As those skilled in the art recognize, Erlenmeyer flask 18 has a wide base 20, with sides 22 that taper upward to a short vertical neck 24. In some embodiments, the mouth 26 of the Erlenmeyer flask 18 may be provided with a beaded lip 28 that can be closed using a rubber stopper 30, or similar.

Apparatus 10 also includes a temperature sensor 32 for determining sample temperature over time. In some embodiments, temperature sensor 32 may be a laboratory thermometer 34. In some embodiments, laboratory thermometer 34 may be a mercury thermometer made in accordance with American Society for Testing and Materials (ASTM) standard ASTM E-1. As shown, laboratory thermometer 34 includes a stem portion 36 and a bulb 38.

In some embodiments, apparatus 10 includes a housing 40 for mounting the motor 12 and associated hardware within. In some embodiments, housing 40 includes a mounting base 42 and a hinged-cover 44. A latch mechanism 46 may be provided for securing and locking the hinged-cover 44 to the base 42.

In some embodiments, a plurality of feet 48 may be provided. In some embodiments, a means to level the apparatus 10 to ensure that the flask 18 is parallel to the surface upon which the apparatus 10 rests may be provided. In some embodiments, the plurality of feet 48 is a plurality of adjustable feet 48. In some embodiments, the plurality of adjustable feet 48 is effective to level the apparatus 10 so that the flask 18 is parallel to the surface upon which the apparatus 10 rests.

In some embodiments, a level (not shown) may be provided to verify that the flask 18 is parallel to the surface upon which the apparatus 10 rests. In some embodiments, the level may be mounted on the hinged cover 44 of the housing 40.

In some embodiments, apparatus 10 includes a power switch 50 for permitting a source of power to be supplied to the motor 12. In some embodiments, the source of power is alternating current, which is accessed through power cord 52. Alternatively, in some embodiments, the source of power is direct current. In some embodiments, the source of direct current is a battery (not shown). In some embodiments, the battery is mounted within the housing 40.

In some embodiments, apparatus 10 may include an indicator 54 to indicate when power is supplied to the motor 12. In some embodiments, indicator 54 is a lamp that illuminates when power is supplied to the motor 12. In some embodiments, power switch 50 and indicator 54 may be combined in a single switch unit 56.

As shown in FIGS. 2 and 3, in some embodiments, to cool motor 12 and prevent the build-up of heat, apparatus 10 may include a vent fan 58. In some embodiments, vent fan 58 may be mounted within an opening 60 of base 42 of housing 40.

As will be described in more detail below, in order to provide proper rotation of the wax-containing sample, such as a petroleum wax-containing sample, and enable the determination of the congealing point of that sample, motor 12 is designed and/or structured and arranged to rotate the clamp 16 at a speed of less than 50 RPM. In some embodiments, the motor 12 is designed and/or structured and arranged to rotate the clamp 16 at a speed of between about 20 RPM and about 30 RPM.

Figure 4:
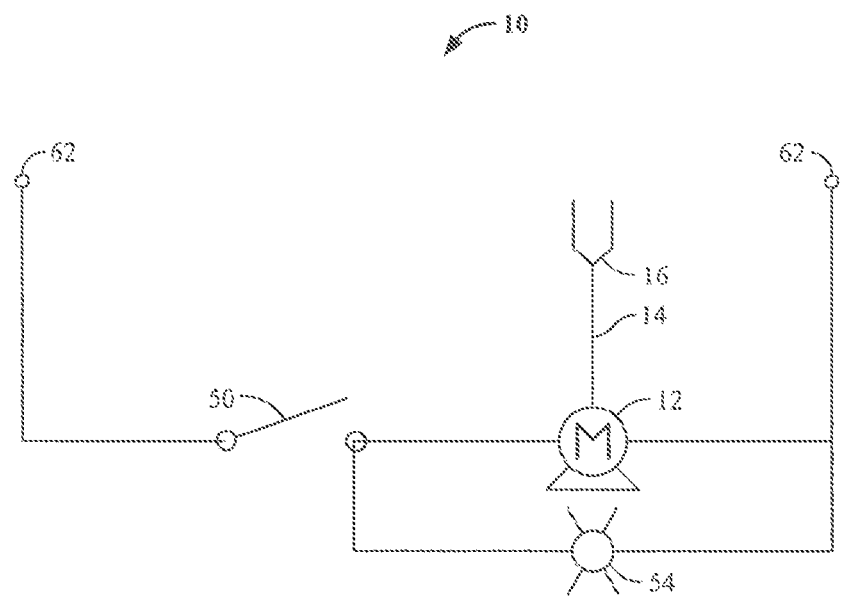
FIG. 4 presents a schematic of an illustrative, nonexclusive example of wiring diagram for the apparatus for determining the congealing point of a wax-containing sample, such as a petroleum wax-containing sample, of the present disclosure.

Referring now to FIG. 4, a schematic of an illustrative, nonexclusive example of a wiring diagram for the apparatus 10 for determining the congealing point of a wax-containing sample, such as a petroleum wax-containing sample, of the present disclosure, is shown. Power is supplied to apparatus 10 across nodes 62. Upon the closure of power switch 50, power is supplied to motor 12, illuminating lamp 54. When powered, rotatable shaft 14 of motor 12 rotates clamp 16. As noted above, in some embodiments motor 12 is designed and/or structured and arranged to rotate the clamp 16 at a speed of less than 50 RPM. In some embodiments, the motor 12 is designed and/or structured and arranged to rotate the clamp 16 at a speed of between about 20 RPM and about 30 RPM.

Figure 5:
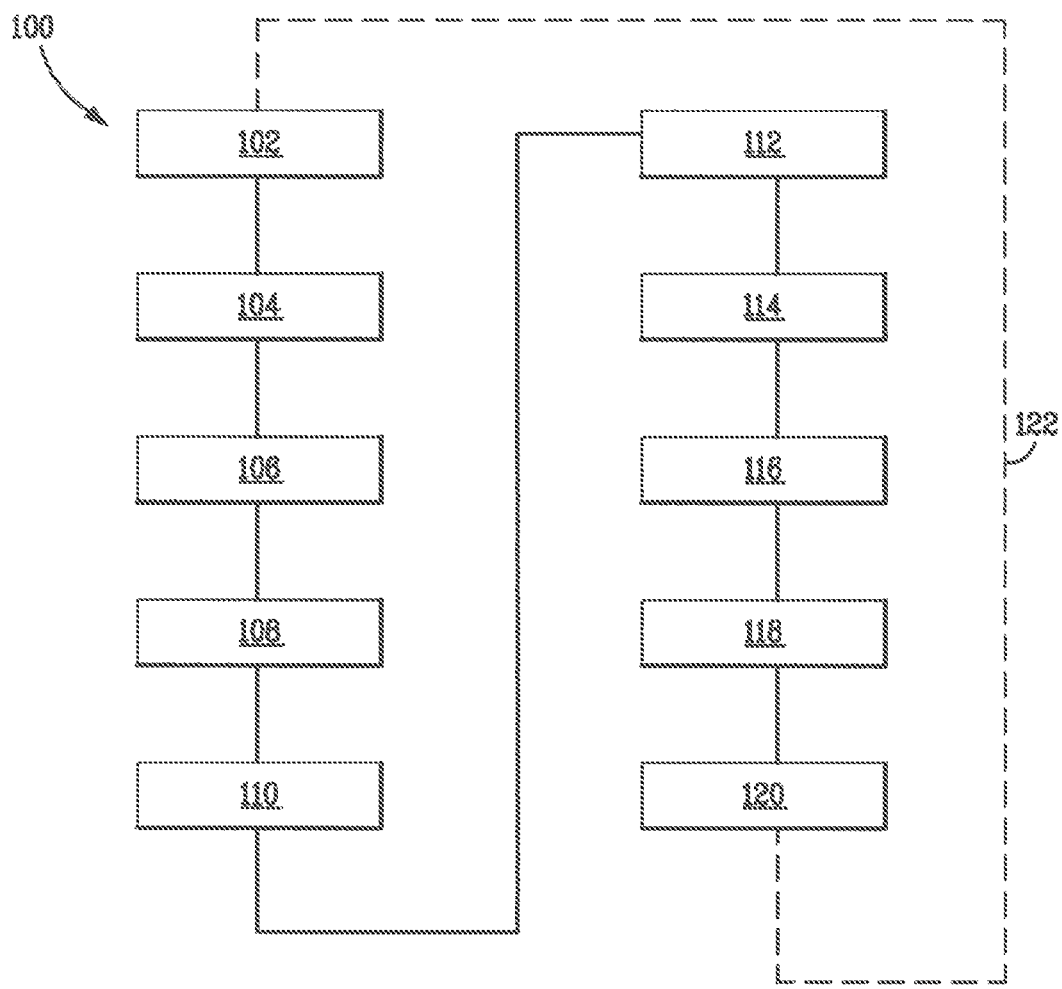
FIG. 5 presents a flow chart of an illustrative, nonexclusive example of a method for determining the congealing point of a wax-containing sample, such as a petroleum wax-containing sample, according to the present disclosure.

Referring now to FIG. 5 a flow chart of an illustrative, nonexclusive example of a method for determining the congealing point of a wax-containing sample 100, such as a petroleum wax-containing sample, according to the present disclosure, is presented. To prepare the wax-containing sample for testing, the method 100 includes the steps of 102, heating a sample flask to a predetermined temperature in a heating unit; 104, heating the wax-containing sample to the predetermined temperature in the heating unit; 106, immersing a temperature sensor in the wax-containing sample; 108, removing the sample flask from the heating unit; 110, removing the temperature sensor from the wax-containing sample, while retaining in adherence thereto a droplet of the wax-containing sample; 112, inserting the temperature sensor into the sample flask; and 114 inserting the sample flask into a mounting clamp of an apparatus for determining the congealing point of a wax-containing sample. As described hereinabove, the apparatus including a motor having a rotatable shaft extending horizontally therefrom, the mounting clamp operatively connected to the rotatable shaft.

To determine the congealing point of a wax-containing sample; method 100 further includes 116, providing a source of power to the motor to rotate the sample flask; 118, monitoring the temperature as the sample flask rotates; and 120, identifying the temperature at which the wax-containing sample congeals.

In some embodiments, the method 100 also includes 122 repeating steps 100-120.

In some embodiments, the method 100 includes rotating the clamp at a speed of less than 50 RPM. In some embodiments, the method 100 includes rotating the clamp at a speed of between about 20 RPM and about 30 RPM.

In some embodiments, the repeatability of the method 100 is at leak about 0.5° C. for petroleum distillate wax-containing samples and at least about 1.0° C. for residual wax-containing samples.

In some embodiments, the reproducibility of the method is at least about 1.5° C. for petroleum distillate wax-containing samples and at least about 2.5° C. for residual wax-containing samples.

As has be described, current manual practices of conducting congealing point testing require an operator to be exposed to multiple risks, including, but not limited to, the handling of hot glassware (about 96° C. to about 102° C.) for extended periods (about 3 to about 8 consecutive minutes, depending upon the sample); the handling of hot liquid-in-glass thermometers for an extended period (about 3 to about 8 consecutive minutes, depending upon the sample); and exposure to Repetitive Stress Injury (RSI) risk if multiple samples are to be tested, since manual testing requires the constant resetting of wrists to rotate Erlenmeyer flask. Moreover, current practices provide no standard means of ensuring that multiple operators are rotating the flask at the same speed. During testing, an operator must manually count rotations while testing, to obtain roughly 1 revolution every 2 to 3 seconds.

As may be appreciated, the apparatus and methods described herein provide a semi-automated alternative to the manual test method provided in ASTM D938, "Standard Test Method for Congealing Point of Petroleum Waxes, Including Petrolatum" and or the method described in the Technical Association of the Pulp and Paper Industry (TAPPI) paper "Congealing Point of Petroleum Waxes Including Petrolatum—Proposed Revision of T 662 SU-66 as a Standard." The apparatus described herein provides an automatic-rotation apparatus that is designed to hold a flask and rotate the flask at a controlled rate. In some embodiments, the flask may be a 125 ml Erlenmeyer flask, which, when used in the methods described herein, may be rotated about a horizontal plane at a rate of about 20 to about 30 rpm to simulate the hand motions described in ASTM D938.

The apparatus and methods described herein provide laboratory technicians and scientists with an ergonomic improvement over manual test methods by eliminating risk of repetitive stress injury (RSI) from constantly resetting the wrist to rotate the flask. Additionally, the apparatus and methods described herein serve to reduce or prevent the burn risk of manual methods by reducing the handling of hot glassware, liquid-in-glass thermometers and hot wax during testing. The apparatus and methods described herein may also provide efficiency gains due to the elimination of the resetting of hands from repetitive motions, enabling more sample throughput. Additionally, increased operational consistency may be achieved as a result of the standardization of rotation speeds by mechanical means.

The apparatus, methods and various embodiments disclosed herein are further illustrated by the following non-limiting Examples.

EXAMPLES

Twenty unique test samples within the scope of ASTM D938, together with four quality control samples, were examined by ASTM D938 and the semi-automatic method disclosed herein, conducted in a manner that conformed to ASTM D938. Thermometers used were identical to those described in Section 6 of ASTM D938 (certified ASTM 54C thermometers, as per Section 6.1). Erlenmeyer flasks (125 ml) of the type described in Section 6.2 were used. Rubber stoppers were bored to allow the ASTM 54C thermometer to fit within the stopper. The height at which the stopper was set on the thermometer was determined as described in Section 7.1.

The procedure was followed as described in Section 7 of ASTM D938. Samples weighing 50±5 g were placed in individual six-ounce metal tins. The rotation speed of the apparatus was maintained at one revolution every 2-3 seconds (20-30 rpm). The apparatus was kept on a lab bench and the thermometer was leveled with respect to the ground. The operator sat in a chair adjusted to allow the lab bench to be at eye-level, thus eliminating any potential neck strain when observing the test.

Samples were obtained from previous ASTM Proficiency Testing Programs cycles and confirmed to be petroleum-based. (ASTM Proficiency Testing Programs (PTP) are statistical quality assurance programs that enable laboratories to assess their performance in conducting test methods within their own laboratories when their data are compared against other laboratories that participate worldwide in the same program.) Samples were first tested as per ASTM D938 manually, followed by testing using the semi-automatic apparatus.

The test results obtained are compared below in Table 1.

TABLE 1

| Oven Temp °C. | Semi-Auto Determination, °C. | | | Avg °C. | Manual Value (D938), °C. | $|\Delta T|$ (Avg-D938) [ASTM R = 1.5° C.] | ASTM PTP Value (If Applicable) | Wax Type |
|---|---|---|---|---|---|---|---|---|
| | #1 | #2 | #3* | | | | | |
| 102 | 52.6 | 52.6 | | 52.6 | 53.0 | 0.4 | — | ASTM PTP Wax 1506 |
| 102 | 71.0 | 72.2 | 72.0 | 71.7 | 72.1 | 0.4 | — | 2500N Slack Wax #1 |
| 102 | 65.0 | 65.0 | | 65.0 | 66.0 | 1.0 | — | 600N Slack Wax #1 |
| 95 | 62.0 | 62.0 | | 62.0 | 62.1 | 0.1 | — | 600N Fully-Refined Wax #1 (QC Sample) |
| 80 | 57.8 | 58.0 | | 57.9 | 57.9 | 0.0 | 58.0 | ASTM PTP Wax 1210 |
| 102 | 71.2 | 73.0 | 72.8 | 72.3 | 72.1 | 0.2 | 71.4 | ASTM PTP Wax 1402 |
| 102 | 72.0 | 72.6 | | 72.3 | 71.2 | 1.1 | 71.5 | ASTM PTP Wax 1410 |
| 102 | 65.0 | 65.4 | | 65.2 | 65.9 | 0.7 | — | 600N Slack Wax #2 |
| 102 | 72.0 | 72.6 | | 72.3 | 73.3 | 1.0 | — | 2500N Slack Wax #2 |
| 102 | 71.0 | 71.0 | | 71.0 | 71.2 | 0.2 | — | 600N Fully-Refined Wax #2 |
| 102 | 55.4 | 55.6 | | 55.5 | 55.3 | 0.2 | 55.3 | ASTM PTP Wax 1310 |
| 102 | 62.2 | 62.0 | | 62.1 | 62.1 | 0.0 | — | 600N Fully-Refined Wax #1 (QC Sample) |
| 102 | 62.2 | 62.0 | | 62.1 | 62.1 | 0.0 | — | 600N Fully-Refined Wax #1 (QC Sample) |
| 102 | 59.4 | 59.4 | | 59.4 | 60.0 | 0.6 | — | 400N Slack Wax |
| 102 | 62.2 | 63.0 | | 62.6 | 62.9 | 0.3 | — | 600N Slack Wax #3 |
| 102 | 66.2 | 66.0 | | 66.1 | 65.9 | 0.2 | — | 600N Slack Wax #4 |
| 102 | 53.4 | 53.2 | | 53.3 | 53.5 | 0.2 | — | 150N Slack Wax #1 |
| 102 | 71.2 | 73.0 | 72.4 | 72.2 | 72.1 | 0.1 | 71.4 | ASTM PTP Wax 1402 |
| 102 | 65.8 | 65.4 | | 65.6 | 65.3 | 0.3 | 65.4 | ASTM PTP Wax 1406 |
| 102 | 75.2 | 75.6 | | 75.4 | 75.0 | 0.4 | 74.3 | ASTM PTP Wax 1502 |
| 102 | 62.0 | 62.2 | | 62.1 | 62.1 | 0.0 | — | 600N Fully-Refined Wax #1 (QC Sample) |
| 102 | 64.4 | 65.8 | 66.0 | 65.4 | 66.4 | 1.0 | 61.4 | ASTM PTP Wax 1110; Industry R 13.77, TPI 0.18. Z-Score 1.0 |
| 102 | 74.4 | 74.4 | | 74.4 | 74.4 | 0.0 | 73.5 | ASTM PTP Wax 1202 |
| 102 | 51.0 | 51.0 | | 51.0 | 51.1 | 0.1 | — | 150N Slack Wax #2 |

*Run only if the difference between #1 and #2 is >1° C., as per ASTM D938 test procedure.

Table 1 shows a summary of the waxes that were tested using the semi-automatic apparatus (Determinations 1, 2 and 3). The average of each determination is compared to the value obtained from conducting the traditional ASTM D938 method.

As demonstrated above, the tests conducted confirmed that the apparatus disclosed herein is capable of producing data within the current ASTM D938 precision statement. The ASTM PTP cross-check samples included in the data set for comparison were all within a Z-Score±2.

The semi-automatic apparatus eliminates the use of hands to rotate the sample. This is a significant improvement over the manual method due to the elimination of potential repetitive stress injury (RSI). This improvement is especially important for low-congealing point wax samples. A sample with a low congealing point can cause discomfort due to the extended time of non-stop wrist rotation (up to 8 minutes or more). Using the semi-automatic apparatus eliminated the constant wrist movement while testing, requiring the operator to only prepare the apparatus and record the result. The reduction in glass handling also helps to reduce glassware injury risk.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and define a term in a manner or are otherwise inconsistent with either the non-incorporated portion of the present disclosure or with any of the other incorporated references, the non-incorporated portion of the present disclosure shall control, and the term or incorporated disclosure therein shall only control with respect to the reference in which the term is defined and/or the incorporated disclosure was originally present.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

It is within the scope of the present disclosure that an individual step of a method recited herein may additionally or alternatively be referred to as a "step for" performing the recited action.

Illustrative, non-exclusive examples of assemblies, systems and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

PCT/EP Clauses:

1. An apparatus for determining the congealing point of a wax-containing sample, the sample placed within a sample flask, comprising: a) a motor having a rotatable shaft extending horizontally therefrom; b) a clamp for mounting the sample flask thereto, the clamp operatively connected to the rotatable shaft; and c) a temperature sensor for determining sample temperature overtime.

2. The apparatus of clause 1, further comprising a housing for mounting the motor within.

3. The apparatus of clause 1 or 2, further comprising a power switch for permitting a source of power to be supplied to the motor.

4. The apparatus of clause 3, wherein the source of power is alternating current.

5. The apparatus of clause 1, wherein the source of power is direct current.

6. The apparatus of clause 5, wherein the source of direct current is a battery.

7. The apparatus of clause 6, wherein the battery is mounted with the housing.

8. The apparatus of clause 3, further comprising an indicator to indicate when power is supplied to the motor.

9. The apparatus of any of clauses 1-8, wherein the motor is structured and arranged to rotate the clamp at a speed of less than 50 RPM.

10. The apparatus of clause 9, wherein the motor is structured and arranged to rotate the clamp at a speed of between 20 RPM and 30 RPM.

11. A semi-automated method for determining the congealing point of a wax-containing sample, comprising: (a) heating a sample flask to a predetermined temperature in a heating unit; (b) heating the wax-containing sample to the predetermined temperature in the heating unit; (c) immersing a temperature sensor in the wax-containing sample; (d) removing the sample flask from the heating unit; (e) removing the temperature sensor from the wax-containing sample, while retaining in adherence thereto a droplet of the wax-containing sample; (f) inserting e temperature sensor into the sample flask; (g) inserting the sample flask into a mounting clamp of an apparatus for determining the congealing point of a wax-containing sample, the apparatus including a motor having a rotatable shaft extending horizontally therefrom, the mounting clamp operatively connected to the rotatable shaft; (h) providing a source of power to the motor to rotate the sample flask; (i) monitoring the temperature as the sample flask rotates; and (j) identify the temperature at which the wax-containing sample congeals.

12. The method of clause 11, further comprising repeating steps (a)-(j).

13. The method of clause 11 or 12, wherein the motor rotates the clamp at a speed of between 20 RPM and 30 RPM.

14. The method of any of clauses 11-13, wherein the repeatability of the method is at least 0.5° C. for petroleum distillate wax-containing samples and at least 1.0° C. for residual wax-containing samples.

15. The method of any of clauses 11-14, wherein the reproducibility of the method is at least 1.5° C. for petroleum distillate wax-containing samples and at least 2.5° C. for residual wax-containing samples.

INDUSTRIAL APPLICABILITY

The apparatus, systems and methods disclosed herein are applicable to the petroleum refining industry.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. A semi-automated method for determining a congealing point of a wax-containing sample, comprising:
   a) heating a sample flask to a predetermined temperature in a heating unit;
   b) heating the wax-containing sample to the predetermined temperature in the heating unit;
   c) immersing a temperature sensor in the wax-containing sample;
   d) removing the sample flask from the heating unit;
   e) removing the temperature sensor from the wax-containing sample, while retaining in adherence thereto a droplet of the wax-containing sample;
   f) inserting the temperature sensor into the sample flask;
   g) inserting the sample flask into a mounting clamp of an automatic-rotation apparatus for determining the congealing point of a wax-containing sample, the automatic-rotation apparatus including a motor having a rotatable shaft extending horizontally therefrom, the mounting clamp operatively connected to the rotatable shaft;
   h) providing a source of power to the motor to rotate the sample flask;
   i) monitoring the temperature as the sample flask rotates; and
   j) identifying the temperature at which the wax-containing sample congeals.

2. The method of claim 1, further comprising repeating steps (a)-(j).

3. The method of claim 1, wherein the automatic-rotation apparatus further includes a power switch for providing the source of power to be supplied to the motor.

4. The method of claim 3, wherein the source of power is alternating current.

5. The method of claim 3, wherein the source of power is direct current.

6. The method of claim 5, wherein a source of direct current is a battery.

7. The method of claim 1, wherein the motor rotates the clamp at a speed of less than 50 RPM.

8. The method of claim 7, wherein the motor rotates the clamp at a speed of between 20 RPM and 30 RPM.

9. The method of claim 1, wherein a repeatability of the method is at least 0.5° C. for petroleum distillate wax-containing samples and at least 1.0° C. for residual wax-containing samples.

10. The method of claim 1, wherein a reproducibility of the method is at least 1.5° C. for petroleum distillate wax-containing samples and at least 2.5° C. for residual wax-containing samples.

* * * * *